(12) United States Patent
Devitt et al.

(10) Patent No.: US 7,271,894 B2
(45) Date of Patent: Sep. 18, 2007

(54) IMAGING SYSTEM FOR ROBOTICALLY INSPECTING GAS TURBINE COMBUSTION COMPONENTS

(75) Inventors: John William Devitt, Maineville, OH (US); Custodio J. S. Ferreira, Goshen, OH (US)

(73) Assignee: General Electric Company, Niskayuna, NY (US)

( * ) Notice: Subject to any disclaimer, the term of this patent is extended or adjusted under 35 U.S.C. 154(b) by 454 days.

(21) Appl. No.: 10/605,469

(22) Filed: Oct. 1, 2003

(65) Prior Publication Data

US 2005/0073673 A1    Apr. 7, 2005

(51) Int. Cl.
*G01N 21/00*    (2006.01)
(52) U.S. Cl. ............... 356/241.1; 356/445; 356/237.1; 318/568.12
(58) Field of Classification Search ............... None
See application file for complete search history.

(56) References Cited

U.S. PATENT DOCUMENTS

| | | | | |
|---|---|---|---|---|
| 5,308,986 A | * | 5/1994 | Walker | 250/370.11 |
| 5,554,318 A | * | 9/1996 | Neumann et al. | 73/36 |
| 5,730,528 A | * | 3/1998 | Allison et al. | 250/459.1 |
| 6,414,458 B1 | * | 7/2002 | Hatley et al. | 318/568.12 |
| 6,485,845 B1 | | 11/2002 | Wustman et al. | 428/633 |
| 6,525,500 B2 | | 2/2003 | Hatley et al. | 318/568.12 |
| 6,633,378 B2 | * | 10/2003 | Doyle, Jr. | 356/241.1 |
| 6,644,917 B2 | * | 11/2003 | Zhao et al. | 415/200 |
| 6,730,918 B2 | * | 5/2004 | Srivastava et al. | 356/70 |
| 6,885,006 B2 | * | 4/2005 | Harrold et al. | 250/372 |
| 6,974,641 B1 | * | 12/2005 | Choy et al. | 250/382 |
| 2003/0101587 A1 | | 6/2003 | Rigney et al. | 298/891 |
| 2003/0115941 A1 | | 6/2003 | Srivastava et al. | 731/181 |
| 2003/0118440 A1 | | 6/2003 | Zhao et al. | 415/118 |
| 2005/0169348 A1 | * | 8/2005 | Chen et al. | 374/161 |

* cited by examiner

Primary Examiner—Layla G. Lauchman
Assistant Examiner—Juan D. Valentin, II
(74) Attorney, Agent, or Firm—Fletcher Yoder

(57) ABSTRACT

A system for in situ inspection of a surface of a hot gas component of a turbine includes a robot having an elongated inspection arm extending toward the surface of the hot gas component; and an inspection head carried adjacent an end of the inspection arm remote from controls for the robot. The inspection head is manipulated by the inspection arm to locate the inspection head adjacent interior wall portions defining the hot gas component including by displacing the inspection head in a generally axial direction and generally radially toward a wall portion of the hot gas component being inspected. The inspection head is configured with a UV system to excite and detect fluorescence from a taggant material disposed in a coating on the hot gas component.

29 Claims, 6 Drawing Sheets

IMAGING SYSTEM FOR ROBOTICALLY INSPECTING GAS TURBINE COMBUSTION COMPONENTS

BACKGROUND OF THE INVENTION

The present invention relates to a robotic inspection system for in situ inspection of gas turbine annular combustion components for the purpose of evaluating the condition of the components.

In gas turbine engines, for example, power turbines, air is drawn into the front of the engine, compressed by a shaft-mounted rotary compressor, and mixed with fuel. The mixture is burned, and the hot exhaust gases are passed through a turbine mounted on a shaft. The flow of gas turns the turbine, which turns the shaft and drives the compressor. The hot exhaust gases flow from the back of the engine, turning a secondary turbine which in turn drives a generator.

During operation of gas turbine engines, the temperatures of combustion gases may exceed 3,000° F., considerably higher than the melting temperatures of the metal parts of the engine, which are exposed to these gases. The metal parts that are particularly subject to high temperatures, and thus require particular attention with respect to cooling, are the hot section components exposed to the combustion gases, such as blades and vanes used to direct the flow of the hot gases, as well as other components such as shrouds and combustors.

The hotter the exhaust gases, the more efficient is the operation of the jet engine. There is thus an incentive to raise the exhaust gas temperature. However, the maximum temperature of the exhaust gases is normally limited by the materials used to fabricate the hot section components of the turbine.

The constant demand for increased operating temperature in gas turbine engines has necessitated the development of ceramic coating materials that can insulate the turbine components such as turbine blades and vanes from the heat contained in the gas discharged from the combustion chamber for extending the life of such components. These ceramic coatings are known in the art as thermal barrier coatings (TBC's).

Defects in the TBC consist primarily of cracks, spalls, and erosion. These defects can be caused by various operational conditions such as thermal and mechanical fatigue, and by contamination from foreign debris in the gas stream. Erosion is caused by the action of the hot gas on the surface. Defects left uncorrected can cause reductions in turbine efficiency or component damage resulting in expensive repairs.

Maintenance costs and equipment availability are two of the most important concerns of a gas turbine operator. Proper maintenance is required to minimize equipment downtime and provide long-term reliable operation. Maintenance inspections of gas turbines are broadly classified as standby, running and disassembly. Disassembly inspections are generally categorized into three types: combustion inspection, hot gas path inspection and major inspection. All three types of inspections require shutdown and disassembly of the turbine to varying degrees to enable inspection and replacement of aged and worn components. The combustion inspection includes evaluation of several components of the combustion system including the transition piece. The transition piece is a thin-walled duct used to conduct high-temperature combustion gases from the combustion chamber to the annular turbine nozzle passage. The transition piece and other combustion components are generally inspected for foreign objects, abnormal wear, cracking, thermal barrier coating TBC condition, oxidation/corrosion/erosion, hot spots/burning, missing hardware and clearance limits. Components which fall outside established threshold limits are replaced to maintain optimum operating conditions for the entire system. If not rectified, these conditions could lead to reduced machine efficiency and damage to the turbine that may result in unplanned outages and significant repair costs.

Removal and installation of transition pieces is the most time-intensive operation of the combustion inspection. This operation contributes most significantly to the combustion inspection outage duration and corresponds directly to time lost producing power. To remove transition pieces, all upstream components must be removed, i.e., fuel nozzles, water injectors and various other hardware. Each transition piece is then dismounted and removed one by one in sequence through two access openings in the turbine casing. It will be appreciated that for certain gas turbines, there can be as many as fourteen transition pieces requiring removal.

To date, recommended practice has been to remove the transition pieces and other combustion components to facilitate inspection and refurbishment. Inspection has consisted primarily of visual methods consisting of the unaided eye with auxiliary lighting. Visual methods in known problem areas have been enhanced with the use of liquid red dye penetrant to improve visibility of small hairline cracking. These inspections have typically been performed offline of the combustion inspection process. Such prior inspection practices have many disadvantages, including the time required for disassembly and installation, the lack of direct retrievable defect data for engineering evaluation and historical comparison and complete reliance on human factors. Accordingly, there is a need for more efficient methods to inspect the transition pieces of the gas turbine combustion systems to minimize outage times while providing an accurate assessment of the condition of each transition piece.

BRIEF DESCRIPTION OF THE INVENTION

In one embodiment, a system for in situ inspection of a surface of a hot gas component of a turbine is disclosed. The system includes a robot having an elongated inspection arm extending toward the surface of the hot gas component; and an inspection head carried adjacent an end of the inspection arm remote from controls for the robot. The inspection head is manipulated by the inspection arm to locate the inspection head adjacent interior wall portions defining the hot gas component including by displacing the inspection head in a generally axial direction and generally radially toward a wall portion of the hot gas component being inspected. The inspection head is configured with a UV system to excite and detect fluorescence from a taggant material disposed in a coating on the hot gas component.

In another embodiment, a system for in situ inspection of a turbine having a transition piece body forming part of each of a plurality of an annular array of combustors for a gas turbine, each combustor having a combustion casing forwardly of the transition piece body thereof is disclosed. The system includes a mount secured to an interior robotic manipulator to an open end of one of the combustion casings forwardly of the transition piece body thereof; an elongated inspection arm extending from the mount toward the one transition piece body of the one combustion casing; and an inspection head carried adjacent an end of the inspection arm remote from the mount within the one transition piece body of the one combustion casing. The inspection head is manipulated by the inspection arm to locate the inspection head adjacent interior wall portions of the transition piece body including by displacing the inspection head in a generally axial direction and generally radially toward a wall portion of the transition piece body being inspected. The inspection head is configured with a UV system to excite and detect fluorescence from a taggant material buried in a thermal barrier coating (TBC) on the transition piece body.

DETAILED DESCRIPTION OF THE INVENTION

Figure 1:
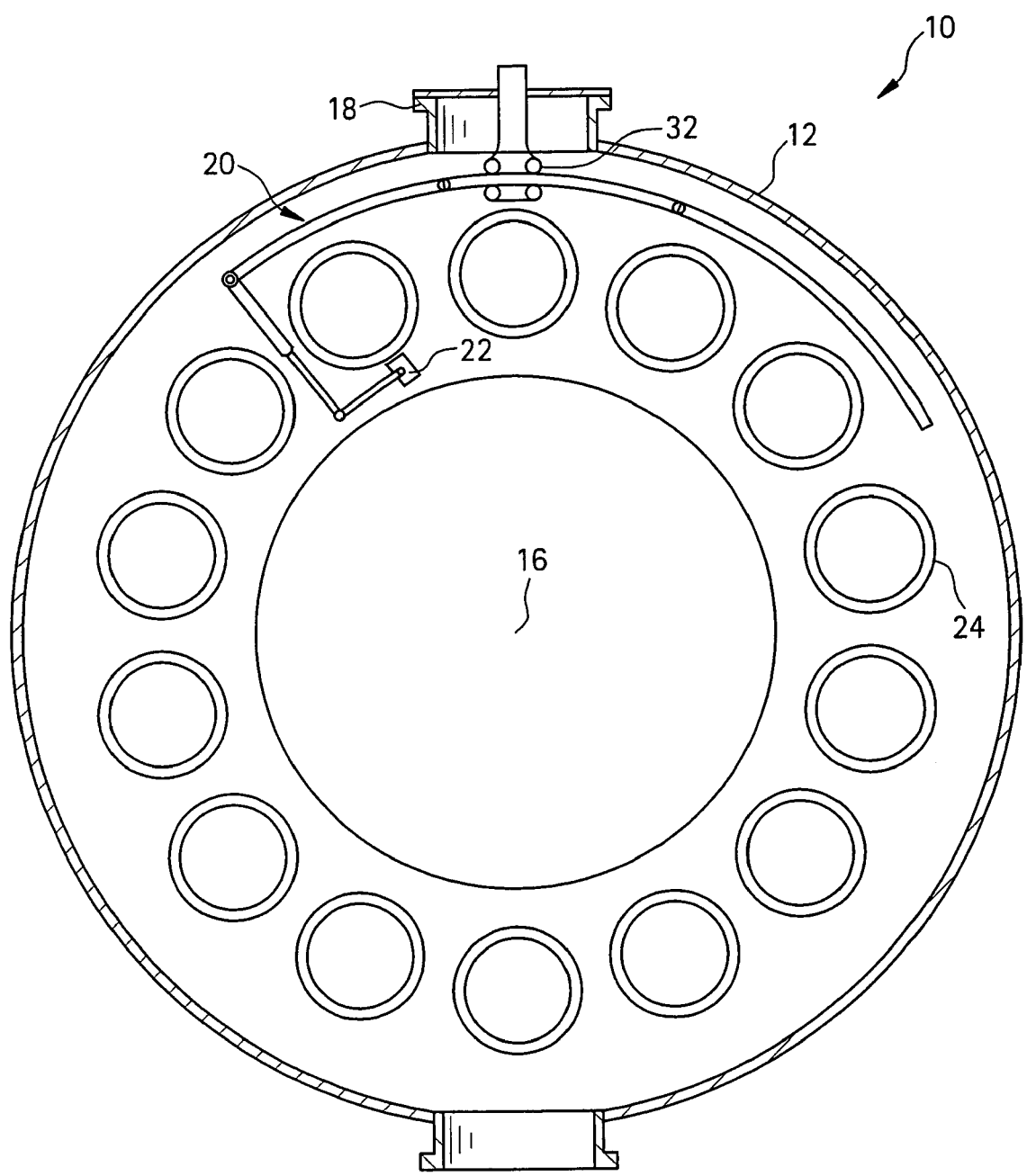
FIG. 1 is a schematic illustration of an annular array of combustors about a gas turbine axis.

Referring now to the drawings, particularly to FIG. 1, there is schematically illustrated an axial view of a gas turbine, generally designated 10, having an outer casing 12 and an annular array of combustors including combustion flow sleeves 14 within the casing 12. The rotational axis of the gas turbine rotor, not shown, is indicated at 16. Also illustrated in FIG. 1 is an access opening or manhole 18 through which an external manipulator, generally designated 20, is inserted for inspecting the external surface of each of the impingement sleeves of the transition pieces. By manipulating the external manipulator 20, an inspection head 22 may be displaced axially the full length of the impingement sleeve as well as positioned at any location about the entire external peripheral surface of the impingement sleeve.

Figure 2:
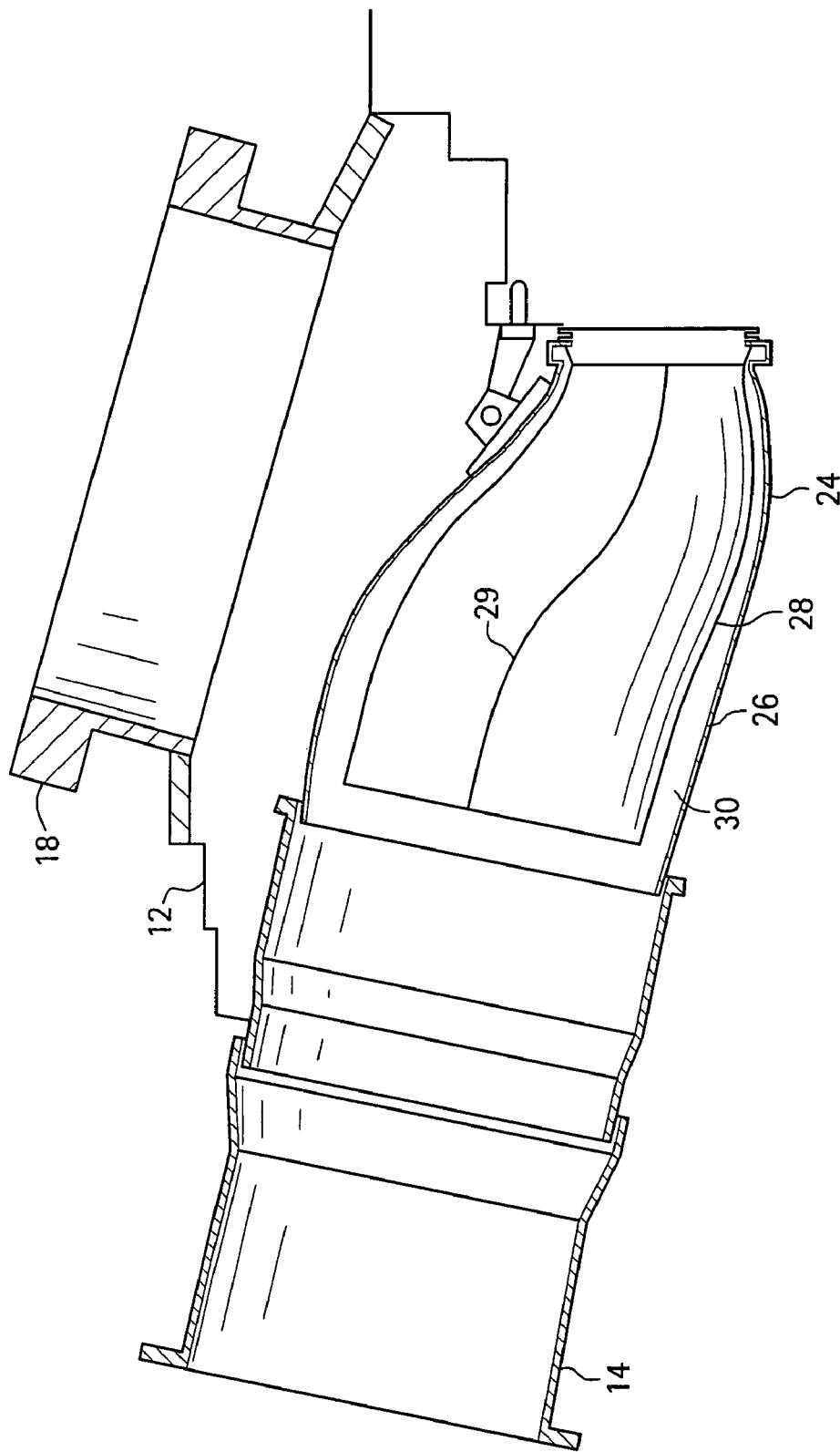
FIG. 2 is a fragmentary side elevational view of a combustor flow sleeve and a transition piece of a combustor illustrating an access opening.

Referring now to FIG. 2, there is illustrated a flow sleeve 14 and a transition piece 24, the transition piece including an impingement, i.e., perforated sleeve 26 surrounding a transition piece body 28. Body 28 extends generally axially from adjacent the forward end of the impingement sleeve 26 and is connected at its rearward end to the first-stage nozzle, not shown, of the gas turbine for flowing hot gases of combustion into the first-stage nozzle. The impingement sleeve 26 and transition piece body 28 are generally circular at their forward ends and flatten out toward their rearward ends, terminating in a generally rectilinear opening for flowing the gases into the first-stage nozzle. The surfaces of the impingement sleeve 26 and transition piece body 28 generally conform with one another and are spaced one from the other, defining a generally annular space 30 between the surfaces of the sleeve and body. As noted previously, the combustion system component and more particularly the transition piece inspection system of the present invention includes three inspection tools, namely: an exterior manipulator, an interior manipulator and an annulus tool. The exterior manipulator is designed to inspect the external surface of the impingement sleeve 26 for damage to the zipper welds, aft brackets and bullhorns. The interior manipulator is designed to inspect the inside surface of the transition piece body 28 for cracking, corrosion and the like and particularly for ensuring that the thermal barrier coating is intact. The annulus tool inspects the exterior surface of the side seam welds 29 securing upper and lower halves of the transition piece body to one another. The exterior manipulator, interior manipulator, and annulus tool are described in detail in U.S. Pat. Nos. 6,525,500 and 6,532,840 to Haley et al. and assigned to the assignee of the present application, the contents of each of which are incorporated herein by reference in their entirety.

Figure 3:
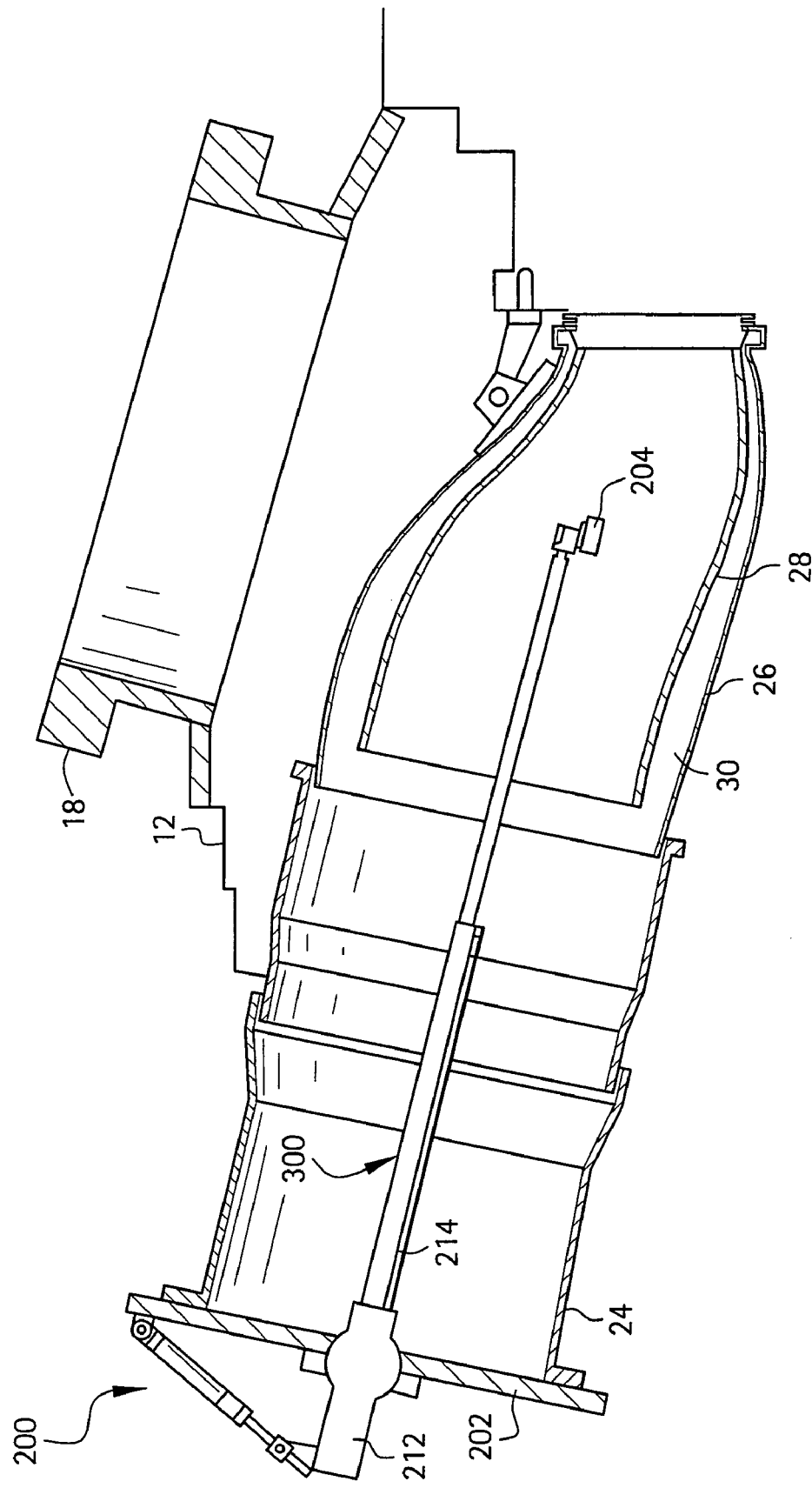
FIG. 3 is a view similar to FIG. 2 illustrating an interior manipulator forming part of an inspection tool according to the present invention.
Figure 4:
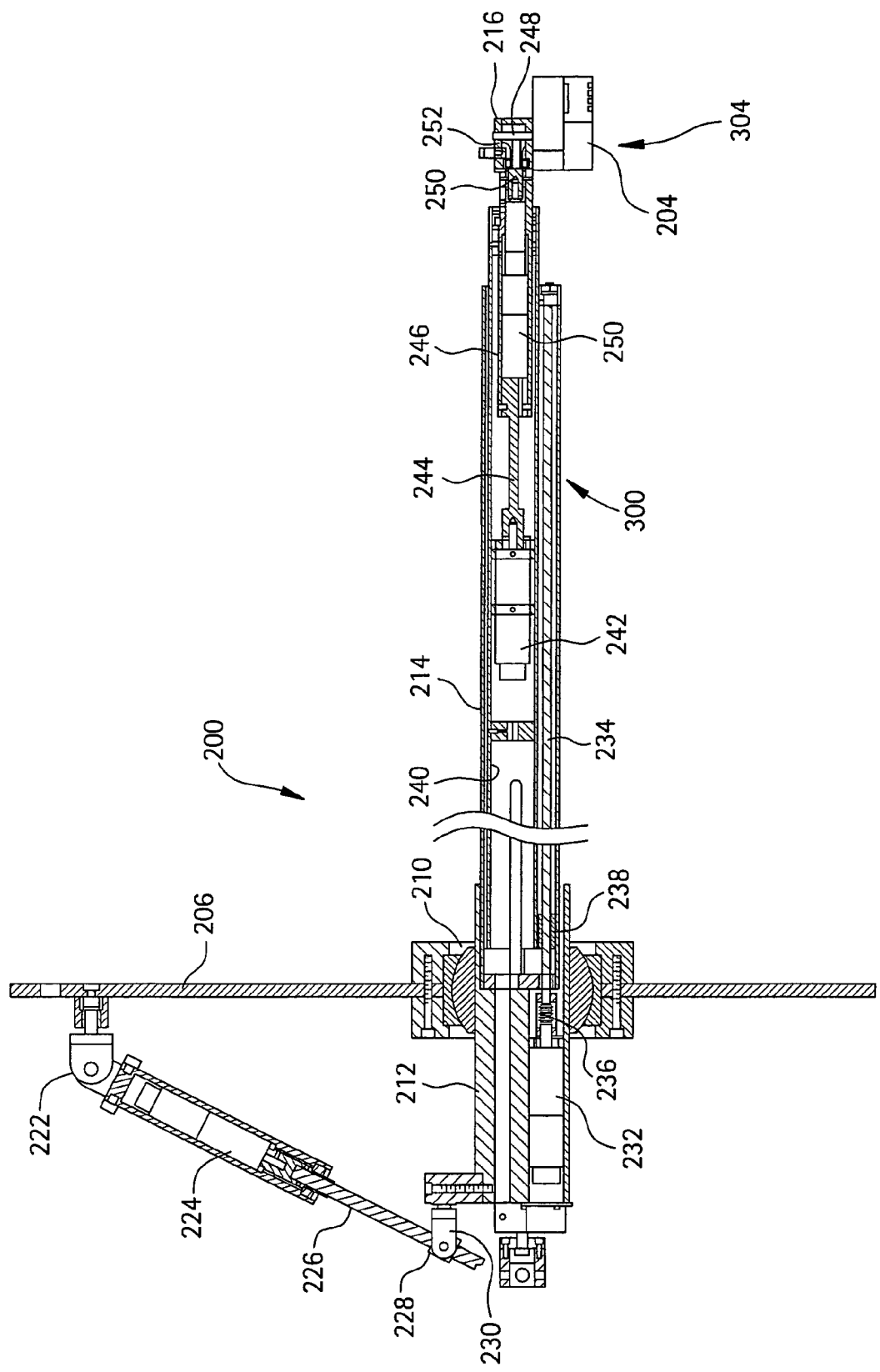
FIG. 4 is an enlarged cross-sectional view of the interior manipulator of FIG. 3.
Figure 5:
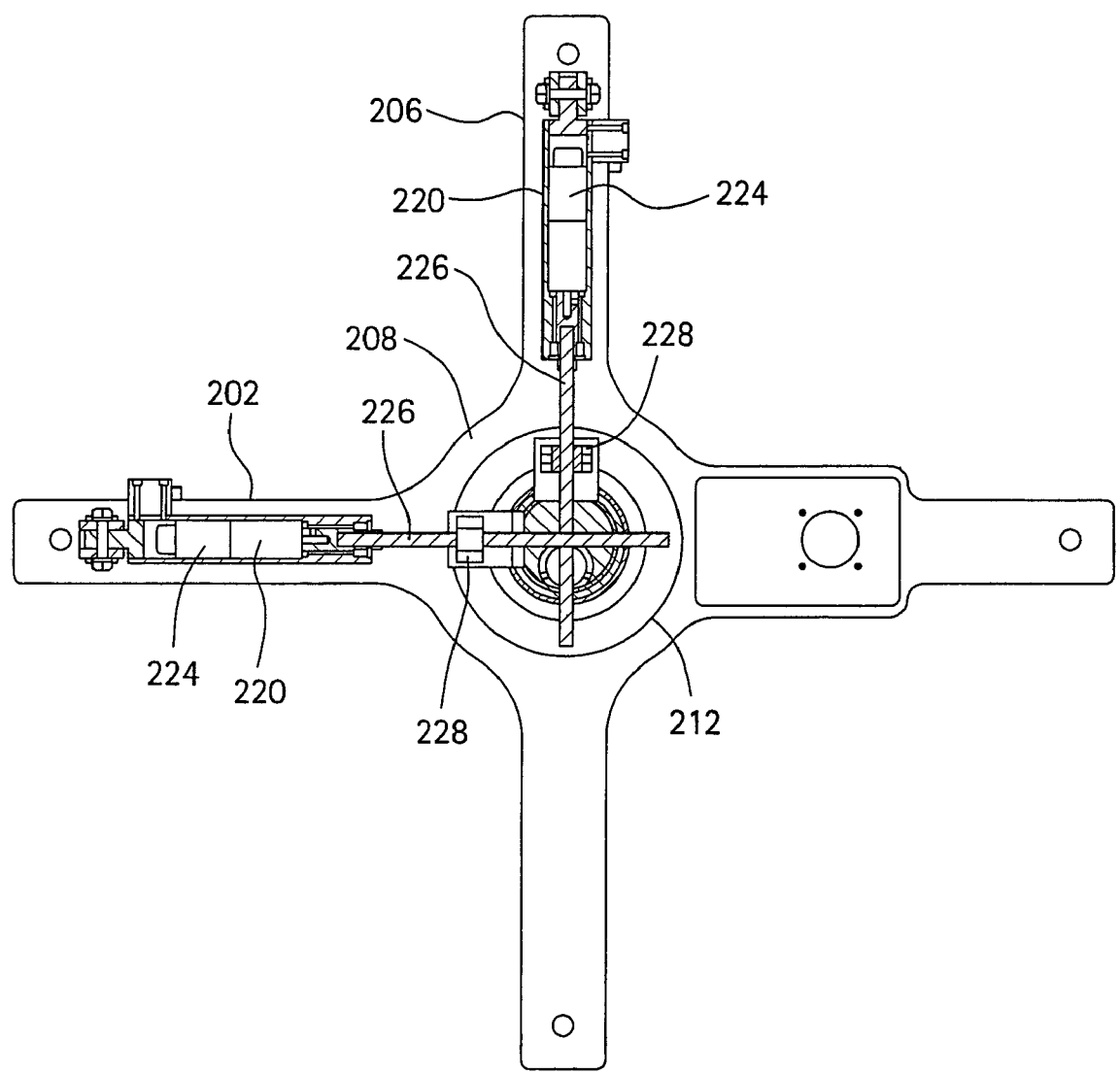
FIG. 5 is an end view of the mounting for the interior manipulator with parts in cross-section.

Referring now to FIGS. 3, 4, and 5, there is illustrated an interior manipulator, generally designated 200, for inspecting the interior surface of the transition piece body 28. Referring to FIG. 3, the interior manipulator 200 includes a mount 202 at one end of the tool and an inspection head 204 at the opposite end of the tool carrying, for example, a similar camera system and light assembly as the exterior manipulator. The mount 202 is in the form of a cross (FIG. 5) having legs 206 90° from one another. The legs 206 are mounted to the flanges of the combustion casing to secure the interior manipulator thereto. The central portion 208 of the mount 202 includes a spherical bearing 210 carried on a tubular section 212 projecting outwardly of the mount 202. On the inside of the mount 202 and carried by the tubular section 212 is an outer tube 214 for carrying the inspection head 204. Mount 202 allows for ease of attachment to the aft casing of the combustion section of the gas turbine.

In order to manipulate the inspection head 204 within the transition piece body 28, a pair of linear actuators 220 are coupled between the outer ends of a pair of legs 206, respectively, and the outer end of the tubular section 212. Particularly, each linear actuator 220 is pivotally secured to a clevis 222 mounted to the outer end of a leg 206. The actuator 220 includes a motor 224 which drives a lead screw 226 engaged in a threaded nut 228 mounted on a hinge 230. The hinge 230 is, in turn, mounted on the tubular section 212. By locating the linear actuators 220 90° apart, it will be appreciated that actuation of the motors 224 pivots the inspection head 204 about the spherical bearing 210 toward and away from the transition piece body 28. There are five servo-controlled axes of motion. These five axes of motion allow the inspection head 204 to get a full view of the interior of the transition piece body 28.

Additionally, by extending or retracting the inspection head 204, the inspection head can be located adjacent any interior surface portion of the transition piece body 28. To accomplish the telescoping movement, a motor 232 is carried by the tubular section 212. Motor 232 drives a lead screw 234 via a shaft coupling 236. A lead screw nut 238 is secured to an inner tube 240 concentric with outer tube 214. By actuating motor 232 and rotating lead screw 234 in engagement with nut 238, tube 240, which mounts the inspection head 204, can be advanced and retracted in an axial direction.

To rotate the inspection head 204 about its own axis, i.e., to pan the inspection head, a pan motor 242 drives a shaft 244, in turn coupled to a tube 246 carrying the inspection head 204. Thus, by actuating motor 242 and rotating shaft 244, tube 246 and head 204 are rotated about the axis of the outer tube 214. To rotate the inspection head 204 about a tilt axis 248, a tilt motor 250 is provided and drives the inspection head about axis 248 through a shaft and beveled gear connection 250 and 252, respectively, similarly as described with respect to the exterior manipulator in U.S. Pat. Nos. 6,525,500 and 6,532,840, incorporated by reference in their entirety. It will be appreciated that the section 212 and tubes, i.e., members 214, 240 and 246 are collectively called inspection arm 300.

The operation of the interior manipulator is believed self-evident from the foregoing description. Upon securing mount 202 of the interior manipulator to the flange of the combustor, actuation of the linear motors 224 and 232 locate the inspection head 204 closely adjacent to a selected interior surface portion of the transition piece body sought to be inspected. By actuating motors 242 and 250, the inspection head is rotated about pan and tilt axes and directed such that the light assembly illuminates the surface portion to be inspected by the video cameras of head 204, discussed more fully below.

When investigating the doping of TBC with materials such as Europia, a rare earth oxide, such that when the TBC is exposed to a specific wavelength, the TBC exhibits phosphorescent properties. A specific UV wavelength, e.g., 254 nm, activates photonic properties of Europia. The resulting visible light is emitted at a wavelength around 610 nm. For example, when one of two TBC materials is 5.0 wt % Europia-doped TBC and both TBC materials are exposed to UV light, the doped TBC and one without, are exposed to normal visible light. As a result of both being exposed to UV light, the effect of the fluorescent dopant (i.e., Europia) is clearly evident when viewed in normal visible light.

TBC coatings play a critical role in the successful operation of turbines. The qualification of such coatings requires extensive testing. After testing, low levels of some contaminants are found to be acceptable in the TBC material. One of the goals therefore, is to employ TBC material with dopant levels below the "contaminant" threshold. Achieving that goal should minimize the effect of the dopant on the TBC and reduce, or eliminate, the testing required to qualify the material. In the case of Europia, the background level in the standard TBC powder is about 0.15 wt %. Quantities of less than about 1 wt % dopant level are likely to have minimal effect on TBC properties.

Therefore, a system is required to detect the presence of low-level impurities that conforms to the geometrical requirements of the transition piece body 28 and the robot arm 300 discussed above. In an exemplary embodiment, such a detection system is incorporated in the inspection head 204 and includes a UV light source, optical filters (for wavelength segregation at the transmission and detection components), and an intensified charge couple device (CCD) camera. In this manner, an imaging system is integrated with the visible light imaging system that is operably coupled to the existing TP Robot arm 300 via inspection head 204 discussed above. The visible light imaging system includes two remote focus micro-cameras, miniature halogen lights and a pair of laser diodes configured to assist with object sizing generally indicated at 304 of inspection head 204 in FIG. 4. In an exemplary embodiment, the vision head or visible light imaging system 304 includes two ¼"CCD cameras; each camera has approximately 280,000 pixels. One camera has a wide-angle lens (f2.2) that allows "overview"; the other camera has a narrow field of view (f4) to provide detailed views of small areas. Each camera can be focused remotely.

Figure 6:
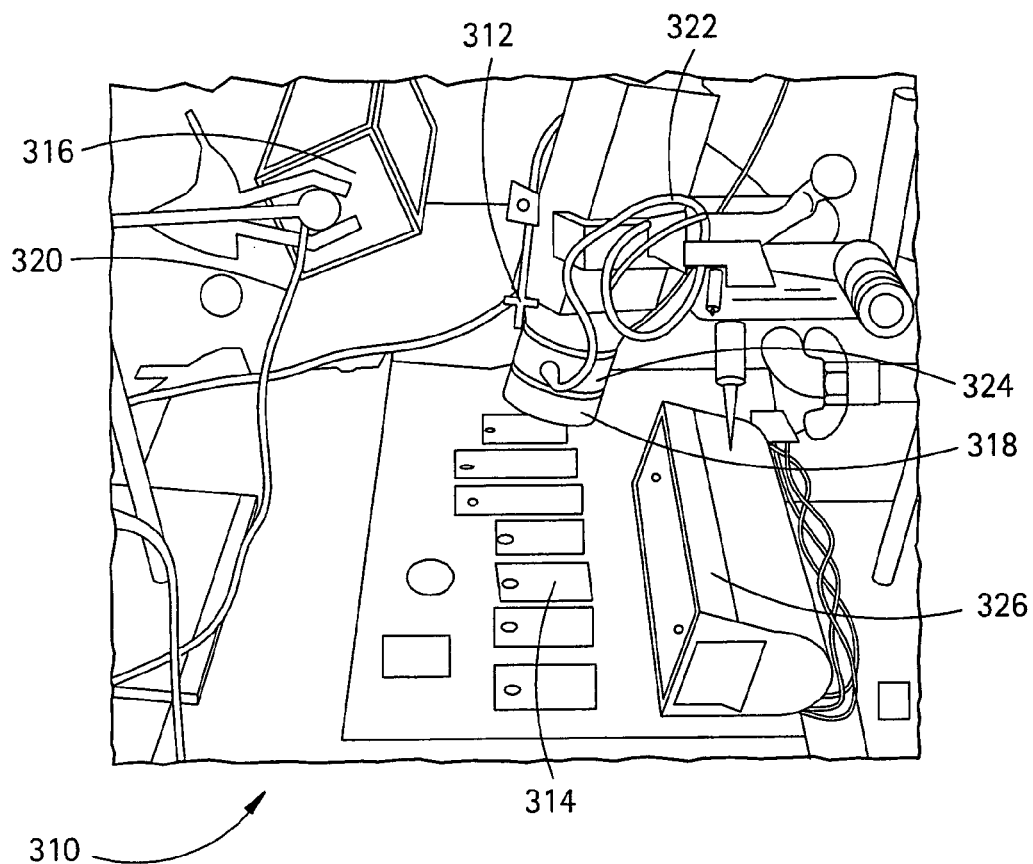
FIG. 6 is a top perspective view of one embodiment of inspection tooling removed from the manipulator including a UV system and visual inspection system set up to image TBC samples having different doped wt %.

Referring now to FIG. 6, one embodiment of an imaging system 310 is shown detached from inspection arm 300. Imaging system 310 includes a standard format color CCD camera 312 configured to determine optical fluorescent emissions from Europia-doped TBC samples 314 when exposed to a low power UV light source 316. In a low light level environment, the fluorescence from samples 314 doped with 2.3 wt %, 5.0 wt %, 8.9 wt % and 19 wt % (bottom four samples as shown) is easily detected when the samples are exposed to UV light from source 316. However samples doped with 0.9 wt % and 0.4 wt % (next two samples as shown) concentrations do not emit sufficient fluorescent light to be detected by a standard ¼" format color CCD camera 312.

To improve the sensitivity of camera 312 to the specific optical emissivity from the exposed taggant samples 314, a 610 nm optical filter 318 with a 10 nm bandwidth is attached to an objective lens of camera 312 and a 254 nm band pass filter 320 is attached to the UV source 316. However, other filters are contemplated between about 254 nm and 300 nm based on the wavelength of UV source 316. This results in improved response for the camera 312 when imaging samples with dopant levels greater than 1 wt %.

In an exemplary embodiment, another camera 322 is used to image taggant samples below 1 wt %. Camera 322 is an intensified camera (e.g.—a Pulnix intensified camera model DN-007). Camera 322 is preferably a black and white digital camera with a built-in intensifier tube. Two camera suppliers include Cohu and Pulnix, but not limited thereto. The Pulnix camera model DN-007 GenIII is preferable based on performance parameters such as its light intensity gain of 10,000× and high-resolution CCD (768H×494V pixels). This camera also has an acceptable weight (14 oz.) and over-all dimensions (1.93"×2.32"×4.73"), for example. Because of the sensitivity of the intensifier tube, this camera preferably includes an objective lens with an auto iris device 324 for protection from intense focused light. In this manner, auto iris device 324 prevents burn-out of the intensifier tube by accidental exposure to bright light. It will also be noted that it was determined that in order to achieve highest sensitivity with the system 310 in FIG. 6, low light levels must be maintained, at least within the filter band pass wavelength range, therefore a supplemental UV light source 326 shown in FIG. 6 is not necessary.

Figure 7:
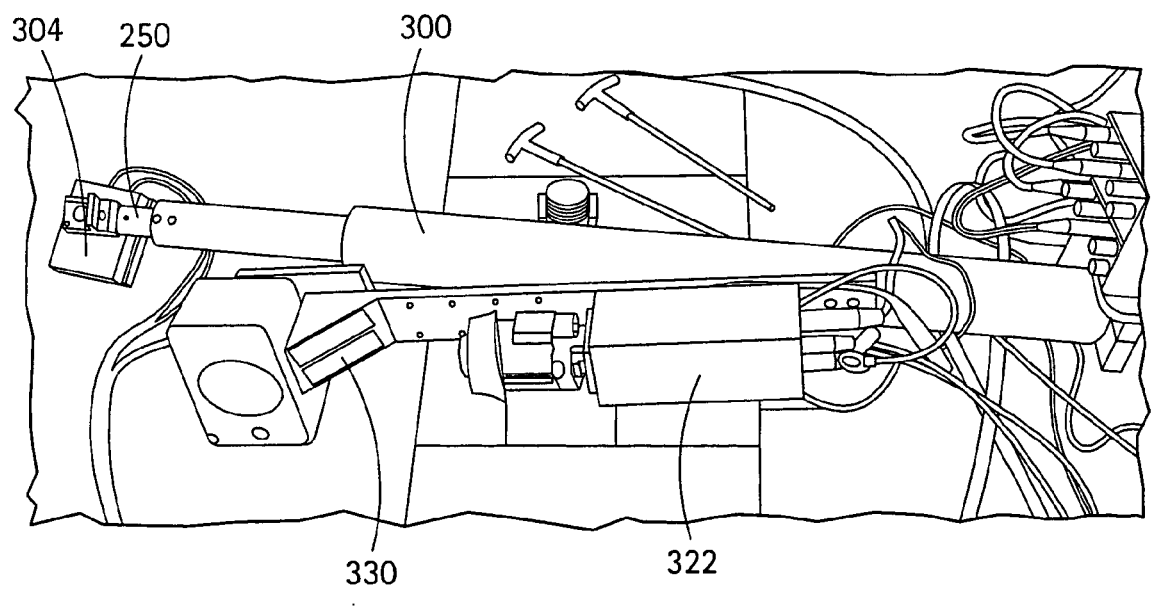
FIG. 7 is an exemplary embodiment of an intensified camera in visual communication with a mirror of the UV system coupled to the interior manipulator of FIGS. 3-5.

FIG. 7 shows intensified camera 322 attached to the robot arm 300. The Pulnix intensified camera 322 is mounted so that it would have a view equivalent to the visible light imaging system. The length of the Pulnix camera 322 does not allow the unit to point directly at the surface of the transition body, however, without hitting the opposing side of the transition body 28. Therefore, a mirror at position 330 (not shown in the figure, only double sided sticky tape) is disposed at about a 45° angle so that the camera 322 can be positioned along the centerline, as shown in FIG. 7, and retrieve similar field of view images as visible light imaging system. Although the intensified camera 322 is compatible with the robot arm 300 as described above, for actual field deployment, the robotic arm 300 is preferably permanently modified to eliminate use of mirror 330 for retrieving images that are substantially normal to a field of view of camera 322. Furthermore, the UV system intensified camera 322 is fiber optically coupled to the collection lens to maintain the compact size and lightweight needed for the robotic arm.

The intensified camera system and UV sensitive taggant system is a significant improvement for inspecting TBC defects. The operator confidence is increased while the time of inspection is diminished significantly. Field implementation of the above described system requires the transition piece body and other turbine components to be coated with TBC doped with a phosphorescent taggant material. The intensified camera is preferably configured or selected to be sensitive to even small additions of the Europia dopant, for example, however, such that extensive re-qualification of the TBC may be avoided, thus minimizing time to full implementation of the system. The above described system is compatible with robotic inspection usage, and therefore is lightweight having a compact head while use of the UV system does not interfere with the visual inspection system. The UV system intensified camera is fiber optically coupled to the collection lens to maintain the compact size and lightweight needed for the robotic arm. This combination of a UV and visual inspection system allows maximum inspection throughput with high sensitivity.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A system for in situ inspection of a surface of a hot gas component of a turbine comprising:
   a robot having an elongated inspection arm extending toward the surface of the hot gas component; and
   an inspection head carried adjacent an end of said inspection arm remote from controls for said robot, said inspection head manipulated by said inspection arm to locate said inspection head adjacent interior wall portions defining the hot gas component including by displacing the inspection head in a generally axial direction and generally radially toward a wall portion of the hot gas component being inspected;
   wherein said inspection head is configured with a UV system to excite and detect fluorescence from a taggant material disposed in a coating on the hot gas component;
   wherein the UV system includes an intensified camera having a built-in intensifier.

2. The system of claim 1, wherein said UV system is configured for simultaneous usage with a visual inspection system on said inspection head.

3. The system of claim 1, wherein said UV system includes a UV light source configured to excite said taggant material with a wavelength between about 254 nm and about 300 nm.

4. The system of claim 1, wherein said intensified camera is configured to detect fluorescence from said taggant material.

5. The system of claim 4, wherein said intensified camera is fiber optically coupled to a collection lens.

6. The system of claim 2, wherein each UV system and visual inspection system camera includes a suitable filter to filter out light generated from a light source for use with the other system camera.

7. The system of claim 6, wherein said suitable filter for a camera of said UV system includes a 610 nm optical filter with about a 10 nm bandwidth operably coupled to an objective lens of the camera configured to protect the camera from stray environmental light.

8. The system of claim 3, wherein a corresponding 254 nm to about 300 nm band pass filter is operably coupled to said UV source.

9. The system of claim 4, wherein said intensified camera is a black and white (CCD) digital camera with a built-in intensifier tube.

10. The system of claim 4, wherein said intensified camera includes an objective lens with an auto iris for protection from intense focused light.

11. The system of claim 4, wherein said intensified camera is operably connected to said inspection arm along an axis defining said inspection arm and is axially aligned therewith such that a mirror is oriented generally at a 45 degree angle for viewing an object normal to a field of view of said intensified camera.

12. The system of claim 1, wherein said UV system is configured to detect at least one of defects as small as 12.5 mm in diameter and defects in said coating with less than about 1% of said taggant material.

13. The system of claim 1, wherein said coating is a thermal barrier coating (TBC).

14. The system of claim 1, wherein said inspection head is configured to rotate about pan and tilt axes relative to said arm.

15. The system of claim 1, wherein the inspection head comprises two remote focus micro-cameras, miniature lights and a pair of laser diodes configured to assist with object sizing.

16. The system of claim 15, wherein the inspection head comprises first and second CCD cameras, wherein the first camera has a wide-angle lens to provide overview of the object and the second camera has a narrow field of view to provide detailed view of small areas of the object.

17. A system for in situ inspection of a turbine having a transition piece body forming part of each of a plurality of an annular array of combustors for a gas turbine, each combustor having a combustion casing forwardly of the transition piece body thereof comprising:
   a mount secured to an interior robotic manipulator and to an open end of one of said combustion casings forwardly of the transition piece body thereof;
   an elongated inspection arm extending from said mount toward the one transition piece body of the one combustion casing; and
   an inspection head carried adjacent an end of said inspection arm remote from said mount within the one transition piece body of the one combustion casing, said inspection head manipulated by said inspection arm to locate said inspection head adjacent interior wall portions of the said transition piece body including by displacing the inspection head in a generally axial direction and generally radially toward a wall portion of the transition piece body being inspected;
   wherein said inspection head is configured with a UV system to excite and detect fluorescence from a taggant material buried in a thermal barrier coating (TBC) on the transition piece body;
   wherein the UV system includes an intensified camera having a built-in intensifier.

18. The system of claim 17, wherein said UV system is configured for simultaneous usage with a visual inspection system on said inspection head.

19. The system of claim 17, wherein said UV system includes a UV light source configured to excite said taggant material with a wavelength between about 254 nm and about 300 nm.

20. The system of claim 17, wherein said intensified camera is configured to detect fluorescence from said taggant material.

21. The system of claim 20, wherein said intensified camera is fiber optically coupled to a collection lens.

22. The system of claim 20, wherein said intensified camera is a black and white (CCD) digital camera with a built-in intensifier tube.

23. The system of claim 20, wherein said intensified camera includes an objective lens with an auto iris for protection from intense focused light.

24. The system of claim 17, wherein said UV system is configured to detect at least one of defects as small as 12.5 mm in diameter and defects in said coating with less than about 1% of said taggant material.

25. A system for in-situ inspection of a surface of a hot gas component of a turbine, comprising:
a robotic arm comprising an inspection head having an intensified camera having a built-in intensifier of a UV based inspection mechanism configured to detect surface defects of the hot gas component, wherein the inspection head is configured to rotate about a pan axis and a tilt axis relative to the robotic arm, and the robotic arm is configured to move the inspection in a generally axial direction and a generally radial direction toward an interior wall portion of the hot gas component.

26. The system of claim 25, wherein the UV based inspection system is configured to excite and detect fluorescence from a taggant material disposed in a coating on the hot gas component.

27. A method for in situ inspection of a surface of a hot gas component of a turbine, comprising:
moving an inspection head in a generally axial direction and a generally radial direction toward an interior wall portion of the hot gas component via a robotic arm coupled to the inspection head; and
operating a UV based inspection system having an intensified camera with a built-in intensifier disposed on the inspection head to detect surface defects of the hot gas component.

28. The method of claim 27, wherein operating the UV based inspection system comprises exciting and detecting fluorescence from a taggant material disposed in a coating on the hot gas component.

29. A system for in situ inspection of a surface of a hot gas component of a turbine comprising:
a robot having an elongated inspection arm extending toward the surface of the hot gas component; and
an inspection head carried adjacent an end of the inspection arm remote from controls for the robot, the inspection head manipulated by the inspection arm to locate the inspection head adjacent interior wall portions defining the hot gas component including by displacing the inspection head in a generally axial direction and generally radially toward a wall portion of the hot gas component being inspected;
wherein the inspection head is configured with an intensified camera having a built-in intensifier to excite and detect fluorescence from a taggant material disposed in a coating on the hot gas component;
wherein the inspection head includes two remote focus micro-cameras, miniature halogen lights and a pair of laser diodes configured to assist with object sizing.

* * * * *